United States Patent [19]

Rohe et al.

[11] Patent Number: 4,968,496

[45] Date of Patent: Nov. 6, 1990

[54] DEODORANTS AND THE PREPARATION AND USE THEREOF

[75] Inventors: Dieter Rohe, Dinslaken; Peter Bubel; Klaus Driemel, both of Duisburg, all of Fed. Rep. of Germany

[73] Assignee: Grillo-Werke AG, Duisburg, Fed. Rep. of Germany

[21] Appl. No.: 218,885

[22] Filed: Jul. 14, 1988

[30] Foreign Application Priority Data

Aug. 11, 1987 [DE] Fed. Rep. of Germany ....... 3726636

[51] Int. Cl.$^5$ ................................................ A61K 7/32
[52] U.S. Cl. ...................................... 424/76.1; 422/5;
424/76.5; 424/76.6; 424/76.7; 562/509
[58] Field of Search ...................... 424/76, 76.1, 76.5,
424/76.6, 76.7; 252/106; 422/5; 562/509

[56] References Cited

U.S. PATENT DOCUMENTS

| | | | |
|---|---|---|---|
| 3,899,476 | 8/1975 | Ward | 260/97.5 |
| 4,127,543 | 11/1978 | Patzchke | 266/23 R |
| 4,172,123 | 10/1979 | Lowicki | 424/67 |
| 4,425,321 | 1/1984 | Jacquet et al. | 424/65 |
| 4,463,157 | 7/1984 | Kersten et al. | 528/68 |
| 4,571,309 | 2/1986 | Lege | 260/400 |

FOREIGN PATENT DOCUMENTS 0046970 8/1981 European Pat. Off.
0071025 2/1983 European Pat. Off.

OTHER PUBLICATIONS

Danzig, O'Donnell, Bell, Cowan and Teeter, J. American Oil Chemists' Society, vol. 34, pp. 136–138 (1957).
Teeter, Bell, O'Donnell, Danzig and Cowan, J. American Oil Chemists' Society, vol. 35, pp. 238–240 (1958).
Fatty Acids-Their Chemistry, Properties, Production, & Uses, edited by Klare S. Markley, Part 5, pp. 3204–3209, 3170–3173, 3273, 3277.
Teeter, O'Donnell, Schneider, Gast & Danzig, "Journal of Organic Chemistry", vol. 22, pp. 512–514 (1957).
Römpps Chemielexikon, Band 5, 1987, p. 3591, "Rizinenfettsäuren".
Chemical Abstracts, vol. 86, 1977, p. 345.
Chemical Abstracts, vol. 93, 1980, p. 306.
Chemiker Zeitung, 110, Feb. 1986, No. 2, "Bindung von Geruchsemissionen bei Abwasser-, Abluft- und Kompostierungsanlagen Teil I-Einfuhrung in die Problematik", H.-W. Hennig et al.
Chemie-Lexikon, 7th Edition Stuttgart 1975, vol. 5, p. 2985, with translation.

*Primary Examiner*—Ellis P. Robinson
*Assistant Examiner*—Archene Turner
*Attorney, Agent, or Firm*—Wegner & Bretschneider

[57] ABSTRACT

Disclosed are deodorants containing the hydrolyzed ene-adducts and Diels-Alder adducts of ricinene fatty acids and maleic anhydride, which preferably additionally contain (a) zinc ricinoleate with zinc compounds of multiply hydroxylated higher fatty acids, oxamines and resin acids and (b) solvents taken from the group of alcohols, optionally with the addition of water, triethanolamine and organic acids.

8 Claims, No Drawings

DEODORANTS AND THE PREPARATION AND USE THEREOF

The present invention relates in its first aspect to deodorants containing hydrolyzed ene-adducts and Diels-Alder adducts of ricinene fatty acids and maleic anhydride.

The invention relates especially to deodorants additionally containing zinc ricinoleate (which may be admixed with zinc compounds of multiply hydroxylated higher fatty acids, oxamines and resin acids), and solvents taken from the group of alcohols, optionally with the addition of water, triethanolamine and organic acids and solubilizers, to the preparation of said deodorants, and to the use of said deodorants in the technical field, and more particularly for the deodorization in sewage treatment plants, disposal areas, household and hospital use, in agriculture, animal breeding, animal utilization and in meat and fish processing plants.

Deodorants of this kind have been known and have been mostly used in cosmetics. Thus, such products are known as aerosols for room spray, deo-spray, deodorant anti-transpiration spray and deodorant foot spray, as well as deodorant shampoos, deodorant shower preparations, deodorant sticks, deodorant creams, deodorant soaps and deodorant rollers.

The most important component of these deodorants is zinc ricinoleate the action of which may be synergistically enhanced by zinc compounds of multiply hydroxylated higher fatty acids, oxamines and resin acids. Such a zinc ricinoleate with synergistic additives has been produced and marketed under the designation of GRILLOCIN HY-77 by Applicants for many years. In the formulations for the cosmetic products there are additionally present solvents and solubilizers. As the solvents there are mostly employed mono- and polyhydric alcohols, optionally with the addition of some water. As the solubilizers sodium diglycol-ricinosulfosuccinate and disodium polyethyleneglycol-ricinosuccinate have proven to be valuable. The solubilizers have been produced and offered by Applicants under the designations of GRILLOSOL 8 C and GRILLOSOL 8 C 12. The preparation of such solubilizers is described in the European Patent Specification No. 0 046 970.

First, it is the object of the present invention to provide deodorants based on zinc ricinoleate which may be admixed with zinc compounds of multiply hydroxylated higher fatty acids, oxamines and resin acids, which deodorants may also be put into use on a larger scale and, more specifically, in the technical field. The technical deodorants are known to be capable of particularly binding mercaptans, thioethers, amines and aldehydes, whereas ketones, alcohols and esters are not bound. However, the deodorant action has not yet been fully elucidated in detail. Nevertheless, it has been ascertained that the effect of odor extinction caused by said deodorants does not reside in covering or converting the respective odors. The odors are bound in response to functional groups, structure and size of the molecules and thereupon are no longer sensorily perceivable. Thereby the limits of efficiency are also predetermined. Branched-chain hydrocarbons, multi-nuclear and substituted aromatics, ketones, alcohols and esters of carboxylic acids are not bound, as has already been mentioned above. Therefore, cosmetic products may also be perfumed by such active substance.

The solubilizers GRILLOSOL 8 C and GRILLOSOL 8 C 12, respectively, are markedly well compatible with the skin and are toxicologically acceptable.

The cosmetic formulations mostly contain from 1 to 5% by weight of zinc ricinoleate with additives, 1.5 to 15% by weight of solubilizers and up to 90% by weight of solvent selected from the group of the monohydric and dihydric alcohols and, optionally, up to 55% by weight of water. However, such aqueous formulations tend to become turbid and undergo precipitations of individual components.

Thus, it was required for the technical use to develop formulations which are stable also at a higher water content and which contain an inexpensive, highly efficient and stable solubilizer.

Thorough investigations have now resulted in the finding that the hydrolyzed ene-adducts and Diels-Alder adducts of ricinene fatty acids and maleic anhydride are excellently suitable to meet these requirements. Thus, deodorants wherein the previously used solubilizers have been replaced by the hydrolyzed ene-adducts and Diels-Alder adducts of ricinene fatty acids and maleic anhydride may also be used on a commercial scale, and more particularly for the deodorization in sewage treatment plants, disposal areas, household and hospital use, in agriculture, animal breeding, animal utilization and in meat and fish processing plants.

Furthermore, it has also been found that already said hydrolyzed ene-adducts and Diels-Alder adducts of ricinene fatty acids and, maleic anhydride themselves, i.e. in the absence of zinc ricinoleate, exhibit a strongly deodorizing activity, more specifically in the case of strong ammonia and hydrogen sulfide smell or emissions of these substances.

Thus, under a first aspect, the present invention relates to deodorants containing the hydrolyzed eneadducts and Diels-Alder adducts of ricinene fatty acids and maleic anhydride.

Under a second aspect, the present invention relates to deodorants containing
 (a) zinc ricinoleate which may be present in a mixture with zinc compounds of multiply hydroxylated higher fatty acids, oxamines and resin acids,
 (b) solvents taken from the group of alcohols, optionally with the addition of water, triethanolamine and organic acids,
in addition to a component
 (c) consisting of a hydrolyzed ene-adduct or Diels-Alder adduct of a ricinene, a fatty acid and maleic anhydride.

The deodorants according to the invention preferably contain
from 2 to 10% by weight of the component (a),
from 4 to 30% by weight of the component (b) and
from 40 to 90% by weight of the component (c).

For technical use it is possible to dilute the deodorants with larger amounts of water so that they already contain more than 60% by weight of water. However, even with those formulations it is advantageous, if mono- or polyhydric alcohols act as solubilizers, emulsifiers and co-emulsifiers. Then, these formulations are stable even at relatively low temperatures down to 0 ° C., and flocculation which normally decreases the efficiency does not occur.

The hydrolyzed ene-adducts and Diels-Alder adducts of ricinene fatty acids and maleic anhydride are novel. They are prepared according to per se known methods, for example by reacting ricinene fatty acids with maleic anhydride at from 120° C. to 180° C. They are subsequently hydrolyzed with water and neutralized using a base. Aqueous sodium hydroxide solution is preferred to be used, while aqueous potassium hydroxide solution, ammonia and/or triethanolamine may also be used. Preferably, the base is first added in a low excess amount in order to complete hydrolysis. Thereafter, the product solution is adjusted to a pH of from 6 to 7 with an organic acid such as citric acid or lactic acid.

The present invention further relates to the process of preparing said deodorants, which process is characterized in that ricinene fatty acids are reacted with maleic anhydride at from 120 ° C to 180 ° C, the reaction product is hydrolyzed with water and neutralized with a base. If desired, the deodorants thus obtained are mixed as solubilizers with per se known deodorants based on (a) zinc ricinoleate with zinc compounds of multiply hydroxylated higher fatty acids, oxamines and resin acids and (b) solvents taken from the group of alcohols, optionally with the addition of water, triethanolamine and organic acids.

For the purposes of the invention there may be used as the ricinene fatty acids highly purified ricinene fatty acids. However, for reason of cost the commercial ricinene fatty acids as marketed by the suppliers thereof may be readily used. These commercial ricinene fatty acids in general contain from 75 to 85% of ricinene acid and from 1 to 3% of saturated fatty acids. The remainder mostly comprises oleic acid and linseed oil fatty acids. The conjugated doubly-unsaturated ricinene fatty acid is basically capable of forming Diels-Alder adducts and ene-adducts side by side. So far it has not been investigated to which extent Diels-Alder adducts and ene-adducts, respectively, are formed. It is crucial that the neutralized ene-adducts and Diels-Alder adducts of ricinene fatty acids and maleic anhydride are non-toxic, do not cause irritations of the mucous membranes, are biodegradable and constitute very efficient solubilizers and emulsifiers having some cleaning effect. Thus, without doubt they may be employed on a commercial scale and alone, by themselves, they already act as strong deodorants.

As solvents there can be employed mono- and polyhydric alcohols, particularly ethanol, isopropyl alcohol, propylene glycol, dipropylene glycol, glycerol and trimethylolpropane. These alcohols contribute in that even in diluted aqueous solutions no precipitation occurs and, thus, deactivation is thereby prevented. Therefore, the diluted aqueous-alcoholic solutions can also be applied through pumps and through nozzles without any clogging.

The deodorants of the invention, the preparation and use thereof are further illustrated by the following Examples.

EXAMPLE 1

Preparation of the hydrolyzed ene-adduct and Diels-Alder adduct of ricinene fatty acid with maleic anhydride 14.5 kg of technical ricinene fatty acid (containing about 80% of ricinene fatty acid, about 17% of a mixture of oleic acid and linseed oil fatty acids and about 2% of saturated fatty acid) are reacted with 16.3 kg of maleic anhydride at from 120° C. to 180° C. The cooled mixture is hydrolyzed with 46 kg of water and neutralized with 15 kg of aqueous sodium hydroxide solution. Then 6.1 kg of triethanolamine are added and the pH is adjusted to pH 6 to 7 using a citric acid solution.

EXAMPLE 2

Deodorant as concentrate 6.2 kg of the commercially available zinc ricinoleate comprising synergistic additives of zinc compounds of polyhydroxylated higher fatty acids, oxamines and resin (GRILLOCIN HY-77), 4.5 kg of 1,2-propyleneglycol and 4.5 kg of propanol-2, 1.6 kg of citric acid and 1.6 kg of triethanolamine are added to and thoroughly admixed with 81.6 kg of stirred, hydrolyzed and neutralized product prepared according to Example 1. The concentrate obtained may be put to various uses.

EXAMPLE 3

100 to 250 g of the concentrate obtained according to Example 2 are added per $m^3$ of sludge before treatment by screw-type centrifuges in sewage plants. A reduction in odor to below the smelling threshold is perceived. An aqueous 1:10 dilution of the concentrate is sprayed onto waste disposal areas. Due to type and intensity of the bad odor, the concentration and/or amount of spray is to be increased or decreased.

EXAMPLE 4

100 g of sulfur (contaminated with mercaptans and disulfides) having a very intensive bad odor are superficially wetted with 0.5 g of the concentrate of Example 2 (diluted with water at a 1:1 ratio). Sensory examination resulted in a finding that the deodorized sulfur is odor-free. From these tests a consumption of about 2.5 kg of deodorant per 1 t of sulfur is calculated. The consumption rate may be further reduced by optimization of the conditions.

EXAMPLE 5

Deodorization of the stench material CA 460

The captioned stench material, which has a strong odor like that of Maggi (seasoning comprising a lovage-extract), is completely deodorized by addition of less than 0.1% by weight of the concentrate of Example 2. Similar good results are observed with onion extract.

EXAMPLE 6

A room spray is obtained by mixing 2% by weight of zinc ricinoleate comprising additives (GRILLOCIN HY 77), 10% by weight of the concentrate according to Example 2, 51% by weight of water, 25% by weight of isopropyl alcohol, 4% by weight of isopropyl myristate, 4% by weight of lactic acid and 4% by weight of triethanolamine. The room spray obtained is excellently suitable for removing bad odors in the household or in hospitals.

Contrary to commercially available odor-improving agents such as Maskomal ®, having a strong ester-like odor, the room spray according to the invention is nearly odorless and binds odors which, specifically, are based on mercaptans and amines.

EXAMPLE 7

The concentrate according to Example 2 is diluted with water in a ratio of from 1:1 to 1:10. The solution obtained may be employed in cleaning water, wash water and in vent air cleaning using a washer system. The preparation removes in an excellent manner the smells occurring in agriculture, animal breeding, animal utilization and in meat and fish processing plants.

EXAMPLE 8

Formulation guide

The sodium compounds of Example 1 prepared from the ricinene fatty acids and maleic anhydride are diluted with water in a ratio of from 1:1 to about 1:10; the dilutions obtained may be used as technical deodorants.

EXAMPLE 9

Recommended formulation

Take 5 to 50% by weight of the compound according to Example 1, 10 to 50 % of alcohols (propanol-2, ethanol, glycerol, polyglycol, ethyleneglycol), balance with water to 100%; the pH is adjusted using citric acid or lactic acid as acids and triethanolamine as base, respectively.

EXAMPLE 10

From 50 to 300 g of the preparations according to the Examples 8 or 9 per m3 of sludge are added to and homogeneously dispersed in the sludge prior to the centrifuge stage in a sewage treatment plant. A reduction in odor to below the conventional smelling threshold is accomplished by using said deodorants. The compositions according to the Examples 8 and 9 are particularly well suited for the deodorization of ammonia and hydrogen sulfide.

We claim:

1. Deodorant comprising a concentrate containing:
   (a) about 40 to 90 percent by weight of a component consisting of a hydrolyzed ene-adduct or Diels-Alder adduct of a ricinene fatty acid and maleic anhydride,
   (b) about 2 to 10 percent by weight of zinc ricinoleate, and
   (c) about 4 to 30 percent by weight of an alcoholic solvent in addition to said component (a).

2. Deodorant according to claim 1, wherein said concentrate is diluted with water whereby the deodorant comprises more than 60 percent by weight of water.

3. Deodorant according to claim 1, wherein said alcoholic solvent is a monohydric or polyhydric alcohol.

4. Deodorant according to claim 3, wherein said alcoholic solvent is a member selected from the group consisting of ethanol, isopropyl alcohol, propylene glycol, dipropylene glycol, glycerol and trimethylolpropane.

5. Method of deodorization which consists essentially of applying to an odoriferous area a deodorizing amount of a deodorant comprising a concentrate containing:
   (a) about 40 to 90 percent by weight of a component consisting of a hydrolyzed ene-adduct or Diels-Alder adduct of a ricinene fatty acid and maleic anhydride.
   (b) about 2 to 10 percent by weight of zinc ricinoleate, and
   (c) about 4 to 30 percent by weight of an alcoholic solvent in addition to said component (a).

6. Method according to claim 5, wherein said concentrate is diluted with water whereby the deodorant comprises more than 60 percent by weight of water.

7. Deodorant according to claim 5, wherein said alcoholic solvent is a monohydric or polyhydric alcohol.

8. Deodorant according to claim 7, wherein said alcoholic solvent is a member selected from the group consisting of ethanol, isopropyl alcohol, propylene glycol, dipropylene glycol, glycerol and trimethylolpropane.

* * * * *

UNITED STATES PATENT AND TRADEMARK OFFICE
CERTIFICATE OF CORRECTION

PATENT NO. : 4,968,496

DATED : November 6, 1990

INVENTOR(S) : Dieter ROHE et al.

It is certified that error appears in the above-identified patent and that said Letters Patent is hereby corrected as shown below:

Col. 6, line 1, claim 7, "Deodorant" should be corrected as --Method--.

Col. 6, line 1, claim 8, " Deodorant" should be corrected as -- Method--.

Signed and Sealed this

Sixteenth Day of February, 1993

Attest:

STEPHEN G. KUNIN

*Attesting Officer*  *Acting Commissioner of Patents and Trademarks*